United States Patent
Hall et al.

(10) Patent No.: US 11,383,072 B2
(45) Date of Patent: Jul. 12, 2022

(54) METHODS AND SYSTEMS FOR SELECTION AND USE OF CONNECTORS BETWEEN CONDUITS

(71) Applicant: Merit Medical Systems, Inc., South Jordan, UT (US)

(72) Inventors: John William Hall, North Salt Lake, UT (US); Craig Nordhausen, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 242 days.

(21) Appl. No.: 15/868,313

(22) Filed: Jan. 11, 2018

(65) Prior Publication Data
US 2018/0193631 A1  Jul. 12, 2018

Related U.S. Application Data

(60) Provisional application No. 62/445,413, filed on Jan. 12, 2017.

(51) Int. Cl.
*A61M 39/10* (2006.01)

(52) U.S. Cl.
CPC ..... *A61M 39/10* (2013.01); *A61M 2039/1077* (2013.01)

(58) Field of Classification Search
CPC ............ A61M 25/002; A61M 25/0023; A61M 39/10; G01B 5/007; G01B 5/025; G01B 5/08; G01B 3/34; G01B 5/25; A61B 5/1075; A61B 50/30
See application file for complete search history.

(56) References Cited

U.S. PATENT DOCUMENTS

| | | | |
|---|---|---|---|
| 117,960 A | 8/1871 | Andrews | |
| 221,864 A | 11/1879 | Robbins | |
| 790,977 A | 5/1905 | Peck | |
| 2,735,699 A | 2/1956 | Chadbourne | |
| 3,357,432 A | 12/1967 | Sparks | |

(Continued)

FOREIGN PATENT DOCUMENTS

| | | |
|---|---|---|
| DE | 4418910 | 12/1995 |
| DE | 29515546 | 3/1997 |

(Continued)

OTHER PUBLICATIONS

International Search Report and Written Opinion dated Jun. 15, 2018 for PCT/US2018/020614.

(Continued)

*Primary Examiner* — Nathan R Price
*Assistant Examiner* — Melissa A Snyder
(74) *Attorney, Agent, or Firm* — Dorsey & Whitney LLP

(57) ABSTRACT

Medical devices including vascular access kits and methods of using the kit are disclosed. In some embodiments, a conduit is measured using an outside diameter measurement apparatus to determine if the conduit is compatible with a connector such that there is a continual lumen between the conduit and the connector. In some embodiments, various outside diameter measurement devices and the methods of their use are disclosed. In some embodiments, the methods of connecting a conduit, and in some embodiments a strain relief structure, to a connector are described.

7 Claims, 12 Drawing Sheets

(56) References Cited

U.S. PATENT DOCUMENTS

| | | | |
|---|---|---|---|
| 3,435,823 | A | 4/1969 | Edwards |
| 3,490,438 | A | 1/1970 | Lavender et al. |
| 3,683,926 | A | 8/1972 | Suzuki |
| 3,790,438 | A | 2/1974 | Lewis et al. |
| 3,814,137 | A | 6/1974 | Martinez |
| 3,818,511 | A | 6/1974 | Goldberg et al. |
| 3,826,257 | A | 7/1974 | Buselmeier |
| 3,853,126 | A | 12/1974 | Schulte |
| 3,882,862 | A | 5/1975 | Berend |
| 3,998,222 | A | 12/1976 | Shihata |
| 4,076,023 | A | 2/1978 | Martinez |
| 4,133,312 | A | 1/1979 | Burd |
| 4,184,489 | A | 1/1980 | Burd |
| 4,214,586 | A | 7/1980 | Mericle |
| 4,318,401 | A | 3/1982 | Zimmernan |
| 4,366,819 | A * | 1/1983 | Kaster ............ A61B 17/11 606/153 |
| 4,427,219 | A | 1/1984 | Madej |
| 4,441,215 | A | 4/1984 | Kaster |
| 4,447,237 | A | 5/1984 | Frisch et al. |
| 4,496,349 | A | 1/1985 | Cosentino |
| 4,496,350 | A | 1/1985 | Cosentino |
| 4,503,568 | A | 3/1985 | Madras |
| 4,517,747 | A | 5/1985 | Morin |
| 4,550,447 | A | 11/1985 | Seiler, Jr. |
| 4,619,641 | A | 10/1986 | Schanzer |
| 4,655,771 | A | 4/1987 | Wallersten |
| 4,723,948 | A | 2/1988 | Clark et al. |
| 4,734,094 | A | 3/1988 | Jacob et al. |
| 4,753,236 | A | 6/1988 | Healy |
| 4,771,777 | A | 9/1988 | Horzewski et al. |
| 4,772,268 | A | 9/1988 | Bates |
| 4,786,345 | A | 11/1988 | Wood |
| 4,790,826 | A | 12/1988 | Elftman |
| 4,822,341 | A | 4/1989 | Colone |
| 4,848,343 | A | 7/1989 | Wallsten et al. |
| 4,850,999 | A | 7/1989 | Planck |
| 4,856,938 | A | 8/1989 | Kuehn |
| 4,877,661 | A | 10/1989 | House et al. |
| 4,898,591 | A | 2/1990 | Jang et al. |
| 4,898,669 | A | 2/1990 | Tesio |
| 4,917,087 | A | 4/1990 | Walsh et al. |
| 4,919,127 | A | 4/1990 | Pell |
| 4,929,236 | A | 5/1990 | Sampson |
| 4,955,899 | A | 9/1990 | Della Corna et al. |
| 5,026,513 | A | 6/1991 | House et al. |
| 5,041,098 | A | 8/1991 | Loiterman et al. |
| 5,042,161 | A * | 8/1991 | Hodge ............ A61B 5/1076 33/501.45 |
| 5,053,023 | A | 10/1991 | Martin |
| 5,061,275 | A | 10/1991 | Wallsten et al. |
| 5,061,276 | A | 10/1991 | Tu et al. |
| 5,064,435 | A | 11/1991 | Porter |
| 5,104,402 | A | 4/1992 | Melbin |
| 5,171,227 | A | 12/1992 | Twardowski et al. |
| 5,171,305 | A | 12/1992 | Schickling et al. |
| 5,192,289 | A | 3/1993 | Jessen |
| 5,192,310 | A | 3/1993 | Herweck et al. |
| 5,197,976 | A | 3/1993 | Herweck et al. |
| 5,251,642 | A | 10/1993 | Handlos |
| 5,282,860 | A | 2/1994 | Matsuno et al. |
| 5,330,500 | A | 7/1994 | Song |
| 5,336,616 | A | 8/1994 | Livesey et al. |
| 5,353,513 | A | 10/1994 | Round |
| 5,361,748 | A | 11/1994 | Matteucci |
| 5,399,168 | A | 3/1995 | Wadsworth |
| 5,405,320 | A | 4/1995 | Twardowski et al. |
| 5,405,339 | A | 4/1995 | Kohnen et al. |
| 5,454,790 | A | 10/1995 | Dubrul |
| 5,474,268 | A | 12/1995 | Yu |
| 5,474,563 | A | 12/1995 | Myler et al. |
| 5,476,451 | A | 12/1995 | Ensminger et al. |
| 5,496,294 | A | 3/1996 | Hergenrother et al. |
| 5,509,897 | A | 4/1996 | Twardowski et al. |
| 5,549,663 | A | 8/1996 | Cottone, Jr. |
| 5,558,641 | A | 9/1996 | Glantz et al. |
| 5,562,617 | A | 10/1996 | Finch, Jr. et al. |
| 5,562,618 | A | 10/1996 | Cai et al. |
| 5,591,226 | A | 1/1997 | Trerotola et al. |
| 5,607,463 | A | 3/1997 | Schwartz et al. |
| 5,624,413 | A | 4/1997 | Markel et al. |
| 5,631,748 | A | 5/1997 | Harrington |
| 5,637,088 | A | 6/1997 | Wenner et al. |
| 5,637,102 | A | 6/1997 | Tolkoff et al. |
| 5,645,532 | A | 7/1997 | Horgan |
| 5,647,855 | A | 7/1997 | Trooskin |
| 5,669,637 | A | 9/1997 | Chitty et al. |
| 5,669,881 | A | 9/1997 | Dunshee |
| 5,674,272 | A | 10/1997 | Bush et al. |
| 5,676,346 | A | 10/1997 | Leinsing |
| 5,743,894 | A | 4/1998 | Swisher |
| 5,755,773 | A | 5/1998 | Schuster |
| 5,755,775 | A | 5/1998 | Trerotola et al. |
| 5,755,778 | A | 5/1998 | Kleshinski |
| 5,792,104 | A | 8/1998 | Speckman et al. |
| 5,797,879 | A | 8/1998 | Decampli |
| 5,800,512 | A | 9/1998 | Lentz et al. |
| 5,800,514 | A | 9/1998 | Nunez et al. |
| 5,800,522 | A | 9/1998 | Campbell |
| 5,810,870 | A | 9/1998 | Myers et al. |
| 5,814,098 | A * | 9/1998 | Hinnenkamp ........ A61F 2/2496 33/512 |
| 5,830,224 | A | 11/1998 | Cohn et al. |
| 5,840,240 | A | 11/1998 | Stenoien et al. |
| 5,851,201 | A | 12/1998 | Ritger et al. |
| 5,866,217 | A | 2/1999 | Stenoien et al. |
| 5,904,967 | A | 5/1999 | Ezaki et al. |
| 5,931,829 | A | 8/1999 | Burbank et al. |
| 5,931,865 | A | 8/1999 | Silverman et al. |
| 5,941,908 | A | 8/1999 | Goldsteen et al. |
| 5,957,974 | A | 9/1999 | Thompson et al. |
| 5,997,562 | A | 12/1999 | Zadno-Azizi |
| 6,001,125 | A | 12/1999 | Golds et al. |
| 6,019,788 | A | 2/2000 | Butters et al. |
| 6,036,724 | A | 3/2000 | Lentz et al. |
| 6,102,884 | A | 8/2000 | Squitieri |
| 6,156,016 | A | 12/2000 | Maginot |
| 6,167,765 | B1 | 1/2001 | Weitzel |
| 6,171,295 | B1 | 1/2001 | Garabedian |
| 6,231,085 | B1 | 5/2001 | Olson |
| 6,245,098 | B1 | 6/2001 | Feeser |
| 6,255,396 | B1 | 7/2001 | Ding et al. |
| 6,261,255 | B1 | 7/2001 | Mullis et al. |
| 6,261,257 | B1 | 7/2001 | Uflacker et al. |
| 6,280,466 | B1 | 8/2001 | Kugler et al. |
| 6,308,992 | B1 | 10/2001 | Mitsui et al. |
| 6,309,411 | B1 | 10/2001 | Lashinski et al. |
| 6,319,279 | B1 | 11/2001 | Shannon et al. |
| 6,338,724 | B1 | 1/2002 | Dossa |
| 6,398,764 | B1 | 6/2002 | Finch, Jr. et al. |
| 6,402,767 | B1 | 6/2002 | Nash et al. |
| 6,428,571 | B1 | 8/2002 | Lentz et al. |
| 6,436,132 | B1 | 8/2002 | Patel et al. |
| 6,536,135 | B2 | 3/2003 | Lipkin |
| 6,582,409 | B1 | 6/2003 | Squitieri |
| 6,585,762 | B1 | 7/2003 | Stanish |
| 6,592,615 | B1 | 7/2003 | Marcade et al. |
| 6,610,004 | B2 | 8/2003 | Viole et al. |
| 6,689,096 | B1 | 2/2004 | Loubens et al. |
| 6,689,157 | B2 | 2/2004 | Madrid et al. |
| 6,692,461 | B2 | 2/2004 | Wantink |
| 6,693,461 | B2 | 2/2004 | Wantink |
| 6,699,233 | B2 | 3/2004 | Slanda et al. |
| 6,702,748 | B1 | 3/2004 | Nita et al. |
| 6,702,781 | B1 | 3/2004 | Reifart et al. |
| 6,706,025 | B2 | 3/2004 | Engelson et al. |
| 6,719,781 | B1 | 4/2004 | Kim |
| 6,719,783 | B2 | 4/2004 | Lentz et al. |
| 6,730,096 | B2 | 5/2004 | Basta |
| 6,733,459 | B1 | 5/2004 | Atsumi |
| 6,740,273 | B2 | 5/2004 | Lee |
| 6,749,574 | B2 | 6/2004 | O'Keefe |
| 6,752,826 | B2 | 6/2004 | Holloway et al. |
| 6,758,836 | B2 | 7/2004 | Zawacki |

(56) References Cited

U.S. PATENT DOCUMENTS

| | | | |
|---|---|---|---|
| 6,786,919 B1 | 9/2004 | Escano et al. | |
| 6,858,019 B2 | 2/2005 | McGuckin, Jr. et al. | |
| 6,926,724 B1 | 8/2005 | Chu | |
| 6,926,735 B2 | 8/2005 | Henderson | |
| 6,976,952 B1 | 12/2005 | Maini et al. | |
| 6,981,987 B2 | 1/2006 | Huxel et al. | |
| 7,011,645 B2 | 3/2006 | McGuckin, Jr. et al. | |
| 7,025,741 B2 | 4/2006 | Cull | |
| 7,036,599 B2 | 5/2006 | Matteucci | |
| 7,044,937 B1 | 5/2006 | Kirwan et al. | |
| 7,101,356 B2 | 9/2006 | Miller | |
| 7,131,959 B2 | 11/2006 | Blatter | |
| 7,211,074 B2 | 5/2007 | Sansoucy | |
| 7,244,271 B2 | 7/2007 | Lenz et al. | |
| 7,244,272 B2 | 7/2007 | Dubson et al. | |
| 7,252,649 B2 | 8/2007 | Sherry | |
| 7,297,158 B2 | 11/2007 | Jensen | |
| 7,351,257 B2 | 4/2008 | Kaldany | |
| 7,399,296 B2 | 7/2008 | Poole et al. | |
| 7,438,699 B2 | 10/2008 | Pecor et al. | |
| 7,452,374 B2 | 11/2008 | Hain et al. | |
| 7,507,229 B2 | 3/2009 | Hewitt et al. | |
| 7,588,551 B2 | 9/2009 | Gertner | |
| 7,607,237 B2 * | 10/2009 | Schafer | G01B 3/34 33/501.45 |
| 7,708,722 B2 | 5/2010 | Glenn | |
| 7,722,665 B2 | 5/2010 | Anwar et al. | |
| RE41,448 E | 7/2010 | Squitieri | |
| 7,762,977 B2 | 7/2010 | Porter et al. | |
| 7,789,908 B2 | 9/2010 | Sowinski et al. | |
| 7,828,833 B2 | 11/2010 | Haverkost et al. | |
| 7,833,214 B2 | 11/2010 | Wilson et al. | |
| 7,846,139 B2 | 12/2010 | Zinn et al. | |
| 7,850,675 B2 | 12/2010 | Bell et al. | |
| 7,850,705 B2 | 12/2010 | Bachinski et al. | |
| 7,922,757 B2 | 4/2011 | McGuckin | |
| D637,500 S * | 5/2011 | Corbin | D10/64 |
| 7,972,314 B2 | 7/2011 | Bizup et al. | |
| 8,079,973 B2 | 12/2011 | Herrig et al. | |
| 8,092,435 B2 | 1/2012 | Beling et al. | |
| 8,097,311 B2 | 1/2012 | Wang et al. | |
| 8,313,524 B2 | 11/2012 | Edwin et al. | |
| 8,388,634 B2 | 3/2013 | Rubenstein et al. | |
| 8,512,312 B2 | 8/2013 | Sage | |
| 8,551,139 B2 | 10/2013 | Surti et al. | |
| 8,690,815 B2 | 4/2014 | Porter et al. | |
| 8,776,387 B1 * | 7/2014 | Butler-Ammar | G01B 3/34 33/512 |
| 8,951,355 B2 | 2/2015 | Boyle, Jr. et al. | |
| 9,278,172 B2 * | 3/2016 | Herrig | A61M 39/1011 |
| 9,642,623 B2 | 5/2017 | Agarwal et al. | |
| 9,731,113 B2 | 8/2017 | Grace et al. | |
| 10,172,673 B2 | 1/2019 | Viswanathan et al. | |
| 2001/0011421 A1 * | 8/2001 | Bakke | G01B 3/34 33/501.45 |
| 2001/0053930 A1 | 12/2001 | Kugler et al. | |
| 2002/0049403 A1 | 4/2002 | Alanis | |
| 2002/0055766 A1 | 5/2002 | Wallace et al. | |
| 2002/0055771 A1 | 5/2002 | Sandock | |
| 2002/0069893 A1 | 6/2002 | Kawazoe | |
| 2002/0099432 A1 | 7/2002 | Yee | |
| 2002/0151761 A1 | 10/2002 | Viole et al. | |
| 2003/0009212 A1 | 1/2003 | Kerr | |
| 2003/0100859 A1 | 5/2003 | Henderson et al. | |
| 2003/0125789 A1 | 7/2003 | Ross et al. | |
| 2003/0131489 A1 | 7/2003 | Hsiao | |
| 2003/0135258 A1 | 7/2003 | Andreas et al. | |
| 2003/0135261 A1 | 7/2003 | Kugler et al. | |
| 2003/0139806 A1 | 7/2003 | Haverkost et al. | |
| 2003/0181969 A1 | 9/2003 | Kugler et al. | |
| 2003/0212385 A1 | 11/2003 | Brenner et al. | |
| 2003/0212431 A1 | 11/2003 | Brady et al. | |
| 2004/0024442 A1 | 2/2004 | Sowinski et al. | |
| 2004/0034377 A1 | 2/2004 | Sharkaway et al. | |
| 2004/0054405 A1 * | 3/2004 | Richard | A61B 17/0643 623/1.36 |
| 2004/0073282 A1 | 4/2004 | Stanish | |
| 2004/0078071 A1 | 4/2004 | Escamilla et al. | |
| 2004/0092956 A1 | 5/2004 | Liddicoat et al. | |
| 2004/0099395 A1 | 5/2004 | Wang et al. | |
| 2004/0147866 A1 | 7/2004 | Blatter et al. | |
| 2004/0193242 A1 | 9/2004 | Lentz et al. | |
| 2004/0215058 A1 | 10/2004 | Zirps et al. | |
| 2004/0215337 A1 | 10/2004 | Hain et al. | |
| 2004/0236412 A1 | 11/2004 | Brar | |
| 2005/0004553 A1 | 1/2005 | Douk | |
| 2005/0062282 A1 | 3/2005 | Rosch et al. | |
| 2005/0137614 A1 | 6/2005 | Porter et al. | |
| 2005/0192559 A1 | 9/2005 | Michels et al. | |
| 2005/0203457 A1 | 9/2005 | Smego | |
| 2005/0209581 A1 | 9/2005 | Butts et al. | |
| 2005/0215938 A1 | 9/2005 | Khan et al. | |
| 2005/0273162 A1 | 12/2005 | Laguna | |
| 2006/0004392 A1 | 1/2006 | Amarant | |
| 2006/0029465 A1 | 2/2006 | Auer | |
| 2006/0058867 A1 | 3/2006 | Thistle et al. | |
| 2006/0064159 A1 | 3/2006 | Porter et al. | |
| 2006/0081260 A1 | 4/2006 | Eells et al. | |
| 2006/0118236 A1 | 6/2006 | House et al. | |
| 2007/0038288 A1 | 2/2007 | Lye et al. | |
| 2007/0078412 A1 | 4/2007 | McGuckin et al. | |
| 2007/0078416 A1 | 4/2007 | Eliasen | |
| 2007/0078438 A1 | 4/2007 | Okada | |
| 2007/0088336 A1 | 4/2007 | Dalton | |
| 2007/0123811 A1 | 5/2007 | Squitieri | |
| 2007/0135775 A1 | 6/2007 | Edoga et al. | |
| 2007/0140797 A1 | 6/2007 | Armstrong | |
| 2007/0142850 A1 | 6/2007 | Fowler | |
| 2007/0161958 A1 | 7/2007 | Glenn | |
| 2007/0167901 A1 | 7/2007 | Herrig et al. | |
| 2007/0168019 A1 | 7/2007 | Amplatz et al. | |
| 2007/0173868 A1 | 7/2007 | Bachinski et al. | |
| 2007/0179513 A1 | 8/2007 | Deutsch | |
| 2007/0191779 A1 | 8/2007 | Shubayev et al. | |
| 2007/0197856 A1 | 8/2007 | Gellman et al. | |
| 2007/0213838 A1 | 9/2007 | Hengelmolen | |
| 2007/0219510 A1 | 9/2007 | Zinn et al. | |
| 2007/0233018 A1 | 10/2007 | Bizup et al. | |
| 2007/0249986 A1 | 10/2007 | Smego | |
| 2007/0249987 A1 | 10/2007 | Gertner | |
| 2007/0265584 A1 | 11/2007 | Hickman et al. | |
| 2007/0293823 A1 | 12/2007 | Sherry | |
| 2007/0293829 A1 | 12/2007 | Conlon et al. | |
| 2008/0009781 A1 | 1/2008 | Anwar et al. | |
| 2008/0027534 A1 | 1/2008 | Edwin et al. | |
| 2008/0132924 A1 | 6/2008 | McGuckin | |
| 2008/0167595 A1 | 7/2008 | Porter et al. | |
| 2008/0221469 A1 | 9/2008 | Shevchuk | |
| 2008/0267688 A1 | 10/2008 | Busted | |
| 2008/0306580 A1 | 12/2008 | Jenson et al. | |
| 2009/0076587 A1 | 3/2009 | Cully et al. | |
| 2009/0099649 A1 | 4/2009 | Chobotov et al. | |
| 2009/0137944 A1 | 5/2009 | Haarala et al. | |
| 2009/0179422 A1 | 7/2009 | Werth | |
| 2009/0187158 A1 * | 7/2009 | Richmond | A61M 39/10 604/414 |
| 2009/0227932 A1 | 9/2009 | Herrig | |
| 2009/0234267 A1 | 9/2009 | Ross | |
| 2009/0318895 A1 | 12/2009 | Lachner | |
| 2010/0154800 A1 | 6/2010 | Chang et al. | |
| 2010/0160847 A1 * | 6/2010 | Braido | A61B 17/11 604/8 |
| 2010/0161040 A1 * | 6/2010 | Braido | A61B 17/32002 623/2.1 |
| 2010/0198079 A1 | 8/2010 | Ross | |
| 2010/0268188 A1 | 10/2010 | Hanson | |
| 2010/0268196 A1 | 10/2010 | Hastings et al. | |
| 2010/0292774 A1 | 11/2010 | Shalev | |
| 2011/0015723 A1 | 1/2011 | Batiste et al. | |
| 2011/0034886 A1 | 2/2011 | Elbe et al. | |
| 2011/0054312 A1 | 3/2011 | Bell et al. | |
| 2011/0060264 A1 | 3/2011 | Porter et al. | |
| 2011/0106019 A1 | 5/2011 | Bagwell et al. | |

(56) References Cited

U.S. PATENT DOCUMENTS

| | | |
|---|---|---|
| 2011/0112482 A1 | 5/2011 | Redd |
| 2011/0196282 A1 | 8/2011 | Kassab |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2013/0060268 A1 | 3/2013 | Herrig |
| 2013/0204275 A1 | 8/2013 | Agarwal et al. |
| 2013/0282108 A1 | 10/2013 | Houston et al. |
| 2013/0338559 A1 | 12/2013 | Franano et al. |
| 2014/0018721 A1 | 1/2014 | Gage et al. |
| 2014/0094841 A1 | 4/2014 | Sutton et al. |
| 2014/0150782 A1 | 6/2014 | Vazales et al. |
| 2014/0155908 A1 | 6/2014 | Rosenblath et al. |
| 2014/0192567 A1 | 7/2014 | Balocco |
| 2014/0257244 A1 | 9/2014 | Johnston et al. |
| 2014/0276215 A1 | 9/2014 | Nelson |
| 2014/0288638 A1 | 9/2014 | Knight et al. |
| 2014/0296822 A1 | 10/2014 | Chartrand |
| 2014/0371779 A1 | 12/2014 | Vale et al. |
| 2015/0051532 A1 | 2/2015 | Tomko et al. |
| 2015/0082604 A1 | 3/2015 | Cully et al. |
| 2015/0094744 A1 | 4/2015 | Aghayev et al. |
| 2015/0150640 A1 | 6/2015 | Boyle et al. |
| 2015/0165496 A1 | 6/2015 | Moreau |
| 2015/0257775 A1 | 9/2015 | Gilvarry et al. |
| 2015/0265393 A1 | 9/2015 | Stonebridge et al. |
| 2016/0030708 A1 | 2/2016 | Casiello et al. |
| 2016/0066954 A1 | 3/2016 | Miller et al. |
| 2016/0120673 A1 | 5/2016 | Siegel et al. |
| 2016/0129177 A1 | 5/2016 | Herrig |
| 2016/0136398 A1 | 6/2016 | Heilman et al. |
| 2017/0020556 A1 | 1/2017 | Sutton et al. |
| 2017/0106128 A1 | 4/2017 | Bagwell et al. |
| 2018/0271637 A1 | 9/2018 | Hall et al. |
| 2019/0015627 A1 | 1/2019 | Hall et al. |
| 2019/0022368 A1 | 1/2019 | Hall et al. |
| 2019/0184151 A1 | 6/2019 | Herrig |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 5714358 | 1/1982 |
| JP | 62112567 | 5/1987 |
| JP | 04507050 | 12/1992 |
| JP | 05212107 | 8/1993 |
| JP | 06105798 | 4/1994 |
| JP | 0984871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |
| KR | 1020110036848 | 4/2011 |
| WO | 198403036 | 8/1984 |
| WO | 1990085509 | 8/1990 |
| WO | 199519200 | 7/1995 |
| WO | 199523553 | 9/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 200238198 | 5/2002 |
| WO | 2004032991 | 4/2004 |
| WO | 2004112880 | 12/2004 |
| WO | 2006026687 | 9/2006 |
| WO | 2007061787 | 5/2007 |
| WO | 2009046994 | 4/2009 |
| WO | 2009059371 | 5/2009 |
| WO | 2009082513 | 7/2009 |
| WO | 2009120400 | 10/2009 |
| WO | 2009145901 | 12/2009 |
| WO | 2010059102 | 5/2010 |
| WO | 2011060386 | 5/2011 |
| WO | 2011153302 | 12/2011 |
| WO | 2012125927 | 9/2012 |
| WO | 2015023460 | 2/2015 |
| WO | 2015100251 | 7/2015 |
| WO | 2015127254 | 8/2015 |
| WO | 2018164945 | 9/2018 |

OTHER PUBLICATIONS

International Search Report and Written Opinion dated Jan. 18, 2019 for PCT/US2018/041821.
Office Action dated Jan. 8, 2019 for U.S. Appl. No. 15/035,626.
Office Action dated Sep. 26, 2019 for U.S. Appl. No. 15/693,010.
Office Action dated Sep. 30, 2019 for U.S. Appl. No. 15/875,194.
Office Action dated Oct. 17, 2019 for U.S. Appl. No. 15/828,040.
Office Action dated Oct. 22, 2019 for U.S. Appl. No. 15/035,526.
Office Action dated Aug. 21, 2019 for U.S. Appl. No. 14/192,567.
International Search Report and Written Opinion dated Jul. 17, 2018 for PCT/US2018/023956.
International Search Report and Written Opinion dated Jun. 22, 2018 for PCT/US2018/014371.
Office Action dated May 24, 2018 for U.S. Appl. No. 14/995,270.
Office Action dated Jun. 4, 2018 for U.S. Appl. No. 14/192,567.
Office Action dated Jul. 11, 2018 for U.S. Appl. No. 14/450,468.
Office Action dated Jul. 19, 2018 for U.S. Appl. No. 15/035,626.
Office Action dated Mar. 29, 2019 for U.S. Appl. No. 14/332,091.
Office Action dated Oct. 1, 2018 for U.S. Appl. No. 14/332,091.
Notice of Allowance dated Oct. 5, 2018 for U.S. Appl. No. 15/093,622.
International Search Report and Written Opinion dated Oct. 30, 2018 for PCT/US2018/042900.
Notice of Allowance dated Nov. 6, 2018 for U.S. Appl. No. 14/995,270.
Office Action dated Dec. 5, 2018 for U.S. Appl. No. 14/450,468.
Office Action dated Dec. 7, 2018 for U.S. Appl. No. 14/192,567.
Office Action dated Nov. 29, 2019 for U.S. Appl. No. 15/934,152.
Notice of Allowance dated Mar. 3, 2020 for U.S. Appl. No. 15/035,626.
Notice of Allowance dated Mar. 11, 2020 for U.S. Appl. No. 15/828,040.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
Notice of Allowance dated Mar. 15, 2010 for U.S. Appl. No. 11/216,536.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.

(56) References Cited

OTHER PUBLICATIONS

Office Action dated Mar. 15, 2018 for U.S. Appl. No. 14/332,091.
Office Action dated May 5, 2010 for U.S. Appl. No. 10/962,200.
Office Action dated Jun. 9, 2016 for U.S. Appl. No. 14/192,567.
Office Action dated Jun. 15, 2017 for U.S. Appl. No. 14/192,567.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Besarab, et al.,Measuring the Adequacy of Hemodialysis Access, Current Opinion in Nephrology and Hypertension, Rapid Science Publishers ISSN ,1996 ,1062-4821.
Coulson, et al.,A Combination of the Elephant Trunk Anastomosis Technique and Vascular Clips for Dialysis Grafts, Surgical Rounds ,Nov. 1999 ,596-608.
Coulson, et al.,Modification of Venous End of Dialysis Grafts: An Attempt to Reduce Neointimal Hyperplasia, Dialysis & Transplantation, vol. 29 No. 1 ,Jan. 2000 ,10-18.
Coulson MD, et al.,Modification of Venous End of Dialysis Grafts: An Attempt to Reduce Neointimal Hyperplasia, Dialysis & Transplantation, vol. 29 No. 1 ,Jan. 2000 ,10-18.
Coulson MD, PHD, et al.,A Combination of the Elephant Trunk Anastomosis Technique and Vascular Clips for Dialysis Grafts, Surgical Rounds ,Nov. 1999 ,596-608.
Kanterman, et al.,Dialysis Access Grafts: Anatomic Location of Venous Stenosis and Results of Angioplasty, Interventional Radiology, vol. 195 No. 1, 195 ,Apr. 1995 ,135-139.
Kumpe, et al.,Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Lin, et al.,Contemporary Vascular Access Surgery for Chronic Haemodialysis, They Royal College of Surgeons of Edinburgh. J.R. Coll, Surg, Edinb., 41 ,Jun. 1996 ,164-169.
Peterson, et al.,Subclavian Venous Stenosis: A Complication of Subclavian Dialysis, The Journal of American Medical Association, vol. 252 No. 24 ,Dec. 28, 1994 ,3404-3406.
Raju M.D., et al.,Techniques for Insertion and Management of Complications, PTFE Grafts for Hemodialysis Access, Ann. Surg., vol. 206 No. 5 ,Nov. 1987 ,666-673.
Sharafuddin, et al.,Percutaneous Balloon-Assisted Aspiration Thrombectomy of clotted ahemodialysis Access Grafts, Journal of Vascular and Interventional Radiology, vol. 7 No. 2 ,Mar.-Apr. 1996 ,177-183.
Office Action dated May 22, 2019 for U.S. Appl. No. 14/450,468.
Office Action dated Jun. 17, 2019 for U.S. Appl. No. 15/035,626.
Office Action dated Jul. 23, 2019 for U.S. Appl. No. 14/332,091.
Office Action dated Apr. 17, 2020 for U.S. Appl. No. 15/875,194.
Office Action dated Apr. 17, 2020 for U.S. Appl. No. 15/934,152.
Office Action dated Apr. 28, 2020 for U.S. Appl. No. 14/192,567.
Office Action dated May 1, 2020 for U.S. Appl. No. 15/693,010.
Office Action dated May 5, 2020 for U.S. Appl. No. 15/910,273.
European Search Report dated Jul. 24, 2020 for EP18738538.0.
Office Action dated Aug. 5, 2020 for U.S. Appl. No. 15/875,194.
Office Action dated Aug. 18, 2020 for U.S. Appl. No. 15/934,152.
European Search Report dated Oct. 2, 2020 for EP18745239.6.
European Search Report dated Oct. 26, 2020 for EP18738538.0.
European Search Report dated Oct. 28, 2020 for EP18771028.0.
Notice of Allowance dated Oct. 2, 2020 for U.S. Appl. No. 15/933,815.
Notice of Allowance dated Aug. 3, 2021 for U.S. Appl. No. 16/033,515.
Office Action dated Sep. 22, 2021 for U.S. Appl. No. 15/875,194.
Office Action dated Oct. 6, 2021 for U.S. Appl. No. 15/934,152.
Office Action dated May 21, 2021 for U.S. Appl. No. 15/826,977.
Office Action dated Jun. 3, 2021 for U.S. Appl. No. 16/039,943.
Office Action dated Jun. 15, 2021 for U.S. Appl. No. 15/934,152.
European Search Report dated Mar. 10, 2021 for EP18835705.7.
European Search Report dated Mar. 22, 2021 for EP18832124.4.
Notice of Allowance dated Mar. 24, 2021 for U.S. Appl. No. 15/910,273.
Office Action dated Mar. 3, 2021 for U.S. Appl. No. 15/934,152.
Office Action dated Mar. 29, 2021 for U.S. Appl. No. 16/033,515.
Office Action dated Apr. 6, 2021 for U.S. Appl. No. 16/284,526.
Office Action dated Apr. 21, 2021 for U.S. Appl. No. 15/875,194.
Office Action dated Dec. 17, 2021 for U.S. Appl. No. 16/039,943.
Office Action dated Feb. 18, 2022 for U.S. Appl. No. 15/875,194.
European Search Report dated Dec. 4, 2020 for 18764826.6.
Office Action dated Nov. 24, 2020 for U.S. Appl. No. 15/826,977.
Office Action dated Nov. 30, 2020 for U.S. Appl. No. 15/910,273.
Office Action dated Dec. 7, 2020 for U.S. Appl. No. 16/033,515.
Office Action dated Dec. 11, 2020 for U.S. Appl. No. 16/039,943.

* cited by examiner

METHODS AND SYSTEMS FOR SELECTION AND USE OF CONNECTORS BETWEEN CONDUITS

RELATED APPLICATIONS

This application claims priority to U.S. Provisional Application No. 62/445,413, filed on Jan. 12, 2017 and titled, "Methods and Systems for Selection and Use of Connectors Between Conduits," which is hereby incorporated by reference in its entirety.

TECHNICAL FIELD

The field of the present disclosure relates generally to medical devices. More specifically, the present disclosure relates to conduits, such as catheters and grafts, which are used to provide access into the body and connectors for coupling conduits. In some embodiments, the present disclosure relates to the selection and use of a connector to couple one or more conduits together.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
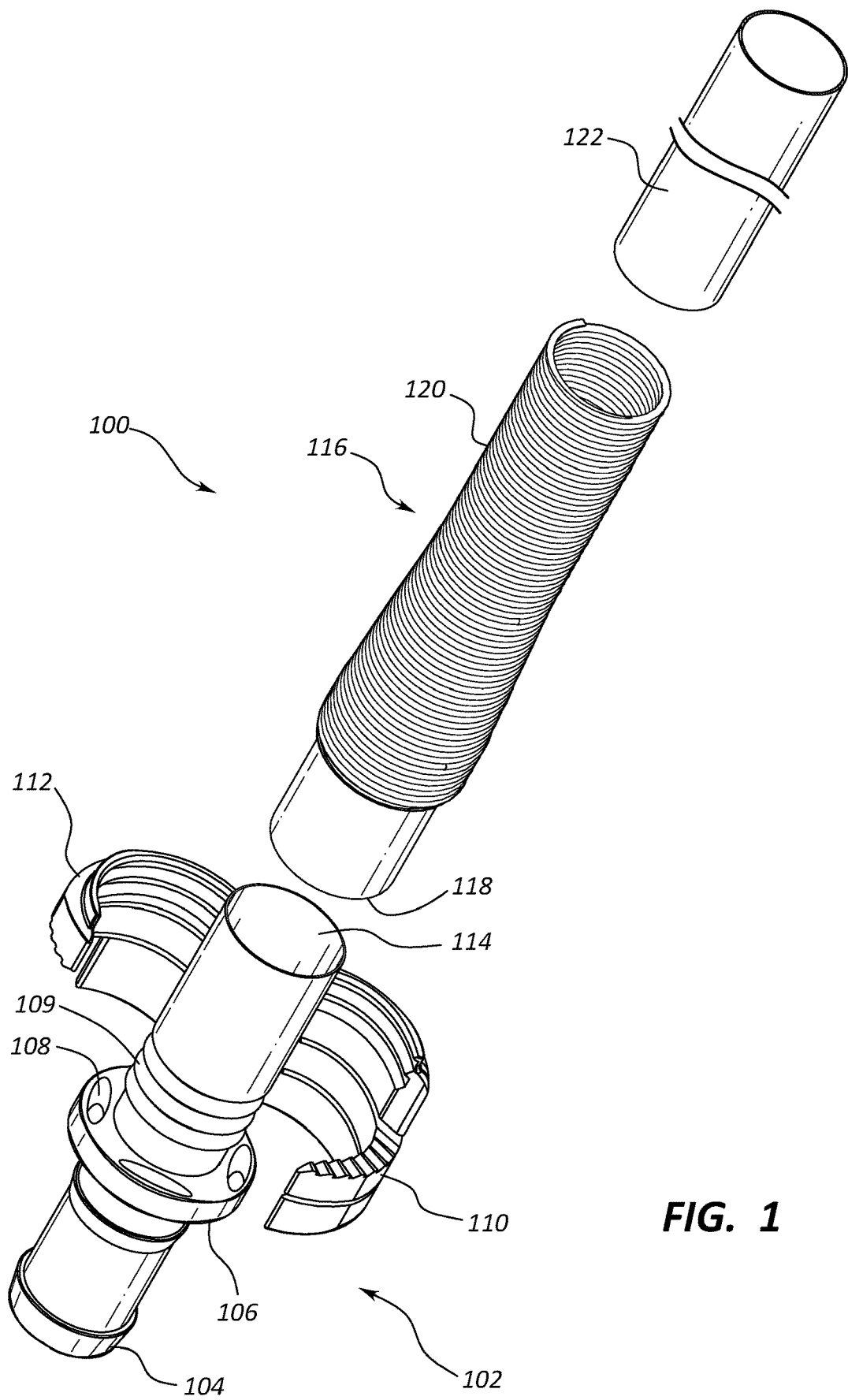
FIG. 1 is a simplified perspective view of certain components of a vascular access system.

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take six to eight weeks before the venous section of the fistula has sufficiently healed and matured to provide adequate blood flow for use with hemodialysis. Moreover, a direct anastomosis may not be feasible in all patients due to anatomical considerations.

Other patients may require the use of artificial graft material to provide an access site between the arterial and venous vascular systems. However, AV grafts still require time for the graft material to mature prior to use, so that a temporary access device must be inserted into a patient for hemodialysis access until the AV graft has matured. The use of temporary catheter access exposes the patient to additional risk of bleeding and infection, as well as discomfort. In addition, patency rates of grafts are still not satisfactory, as the overall graft failure rate may be high. Failure of these grafts is usually due to stenosis at the venous end. These failure rates are further increased in higher-risk patients, such as diabetics, in whom the vascular access is most needed. These access failures result in disruption in the routine dialysis schedule and create hospital costs of over $2 billion per year.

To address these problems various vascular access systems and methods have been developed, as in U.S. Pat. No. 8,690,815 to Porter et al., and U.S. Pat. No. 9,278,172 to Herrig. In such vascular access systems and methods it may be advantageous to use multiple conduits to improve anastomosis with the vasculature and extravascular flow properties. When using multiple conduits, such as multiple artificial vascular catheters, that are connected to each other in the body the conduits may not be labeled with outside diameter measurements. Conduits may be labeled according to the inside diameter of the conduit and, as wall thickness and other parameters may vary between conduits of different design or manufacture, the outside diameter may not consistently relate to the stated inside diameter. Further, in some instances a physician may elect to use a more rigid catheter for one section of the artificial extravascular conduit system, and a more pliable graft for a different section of the same system. If the connector does not accommodate the various conduits, there may be a disruption in the laminar flow of fluid, e.g. blood, through the system. If the fluid is blood, turbulent flow could lead to extensive complications, including thrombosis, which may have significant negative impact on patient morbidity and mortality. Furthermore, in many instances the type and construction of a desired conduit may depend on patient anatomy, therapy type, doctor preference, and so forth. Ability to determine the outside diameter of a conduit may thus facilitate flexibility before and during procedures by allowing a practitioner to determine the needed connector size after selecting a conduit according to factors such as those discussed above.

Connector systems may comprise strain relief components to minimize kinking of a flexible conduit at the interface between a conduit and a connector. Strain relief systems are described in U.S. Pat. No. 9,278,172. The strain relief structure may comprise an elastomeric sleeve that can be slid over a portion of an end of the connector and a coil that can be slid over an end of the conduit. This sleeve and coil may reduce or minimize kinking or pinching of the conduit due at the conduit/connector interface. These strain relief structures may be made of a number of different materials with different resiliency characteristics. The materials used in the strain relief structure may make it difficult to slide or otherwise fit the strain relief structure over an end of the conduit without deforming or otherwise damaging the strain relief structure itself or the conduit.

In the following detailed description, reference is made to the accompanying drawings which form a part hereof and, in which are shown by way of illustration, specific embodiments of the disclosure that may be practiced. These embodiments are described in sufficient detail to enable those of ordinary skill in the art to practice the invention, and it is to be understood that other embodiments may be utilized, and that structural, logical, and electrical changes may be made within the scope of the disclosure. From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In this description, specific implementations are shown and described only as examples and should not be construed as the only way to implement the present disclosure unless specified otherwise herein. It will be readily apparent to one of ordinary skill in the art that the various embodiments of the present disclosure may be practiced with numerous other vascular access solutions. The devices and methods described herein could be useful in a number of environments that employ conduits used or implanted into the body, such as vascular access devices, ventricular assist devices, total artificial hearts, and various types of hemodialysis systems. It would be apparent to one of ordinary skill in the art that the present disclosure may be practiced in any situation that uses multiple conduits, not just fluid or blood conduits. The environments in which the present disclosure may be practiced include short-term applications, e.g. several days to weeks, and longer-term applications, e.g. months to years.

Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method, but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

While the disclosure is susceptible to various modifications and implementation in alternative forms, specific embodiments have been shown by way of non-limiting example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method, but are merely idealized representations employed to more clearly and fully depict the present invention defined by the claims below.

Vascular access systems may be designed and constructed as a single-piece, integrated device, or a multi-piece device comprising separate components that are later joined together. Some embodiments of multi-piece devices are discussed in U.S. Pat. No. 8,690,815 to Porter et al. A multi-piece device may allow an end user, such as a physician, to remove one or more components after they have been implanted in a patent. This may be advantageous if particular components in the vascular access system fail from, for example, thrombus formation or stenosis. It would allow for some components and not the entire vascular access system to be removed.

The connectors or interfaces where the separate components of a multi-piece device are joined or attached, are potential sources of turbulent flow within in the lumen of the system. Any indentation or protrusion into or out of the lumen may cause a disruption of flow. In embodiments in which the multi-piece device is a vascular access system, this turbulent flow may disrupts the normal laminar flow of blood. Disruption in the laminar flow of blood creates a potential risk for thrombus development or hemolysis. Thus, in some instances, connectors, and the various components of a multi-piece device, are designed to maintain smooth laminar flow between components through the connector, and also resist creep or separation of the joined components. Such a connector system may be used with AV grafts, peripherally inserted central catheters (PICC), implantable infusion catheters with and without fluid reservoirs, implantable infusion pumps, left ventricular assist devices, and any other device configured to provide laminar flow from one end of a multi-piece device to the other end of the multi-piece device. In addition to joining fluid conduits, the connector may be used to join conduits to other devices such as reservoirs and needle access ports.

The connector may comprise a biocompatible and/or hemocompatible material. The connector may be used for attaching two conduits which may or may not have different internal and/or outer diameters. In some embodiments, the connector provides a lumen with a smooth fluid path from one end of the multi-piece device to the other. In some embodiments, the connector may have a securing system and/or connecting member to secure a conduit to the connector, which resists disconnection, migration, or separation of the joined components. The connecting member on the connector may be pivotably coupled to a flange on the connector. In some embodiments the connecting member may be any securing device such as clips, rings, sutures, wires, C-shaped clamshell, snap fits, or other mechanical interfits.

In some embodiments, the muli-piece device may comprise a strain relief structure, which is configured to resist occlusion and kinking along portions of a conduit attached to the device. A strain relief structure may be used in connection with any vascular access system including flexible segments such as those comprising polytetrafluoroethylene (PTFE), silicone, polyurethane, or other materials. In some embodiments, one side of a connector may be pre-connected to a component of the multi-piece device to the connector before the start of the surgery, for example a connector may be coupled to one conduit before therapy begins. In some embodiments, a procedure may also comprise selecting a suitably sized connector for the conduits chosen by the end user, which may have different internal and/or outer diameters. As further outlined below, in some embodiments a kit is provided an end user with a plurality of differently sized connectors, or a plurality of different connecting members to be used with various connectors.

FIG. 1 depicts one embodiment of a multi-piece vascular access system 100 that may be configured to shunt blood from a first vascular lumen to a second vascular lumen. The vascular access system 100 can take any suitable form, and in some embodiments is adapted to be implanted subcutaneously within an animal, more specifically a mammal, and still more specifically a human. The vascular access system 100 may be implanted subcutaneously and extravascularly. The vascular access system 100 may be configured to improve or maximize laminar flow through the lumen, and to minimize or eliminate potential turbulent flow through the system, more specifically blood passing through the system. The vascular access system 100 may be configured to join a first artificial conduit with a first outside diameter, to a second artificial conduit with a second outside diameter in such a way that there is a continuous lumen between the two conduits. Some embodiments of the vascular access system 100 comprise a connector 102 which may be used to couple a first artificial conduit with a first outside diameter, to a second artificial conduit with a second outside diameter. In an alternative embodiment the first artificial conduit and the second artificial conduit have the same outside diameter.

In an embodiment of the vascular access system 100, the system comprises a connector such as connector 102, to join a first artificial conduit, such as conduit 122, with a second artificial conduit (not shown). The connector 102 may comprise various forms, such as, but not limited to, a clamshell connector, a suture, or tension clips. In another embodiment the connector 102 is capable of joining a single artificial conduit. In still another embodiment the properly sized connector is selected to join the conduit before the physician implants it in a patient. Methods of selecting the properly sized connector are discussed in more detail below.

In one embodiment, connector 102 comprises a first end 114 with an outside diameter configured to engage with a first end of an artificial conduit, such as conduit 122. The connector 102 may further comprise a second end 104 and a flange 106. In some embodiments, the flange 106 comprises holes 108 through which grasping tools or suture may be passed as will be discussed in greater detail below. In another embodiment, the connector 102 may comprise a plurality of connecting members. In one embodiment, the connecting member may comprise a first securing structure 112 pivotably coupled with flange 106 and a second securing structure 110 pivotably couple with flange 106, such that the two securing structures are configured to close over the first end 114 of the connector to securely fasten, at least a conduit, such as conduit 122, to the connector 102.

In another embodiment of FIG. 1, the connector 102 comprise ridges 109 on the body of the connector closest to the flange 106. These ridges 109 are configured to more securing hold the conduit 102 when an end user slides it onto first end 114 of connector 102. In one embodiment, the first securing structure 112 and the second securing structure 110 are configured to close over at least conduit 102 once the end user slides it over first end 114 of connector 102, and are configured to compress the conduit against ridges 109 to create more engagement with the connector 102.

In the embodiment of FIG. 1, the vascular access system 100 comprises a connector 102, a strain relief structure 116, and at least one artificial conduit, such as conduit 122. The strain relief structure 116 is configured to slide over an artificial conduit. In some embodiments, the strain relief structure 116 comprises a first end 118 that can slide over a portion of the first end 114 of a connector, such as connector 102. The first end 118 of the strain relief structure 116 may comprise an elastomeric sleeve. The strain relief structure 116 may also comprise a second end 120 that surrounds the conduit 122 to reduce strain concentrations at the interface between the conduit 122 and the connector 102. In the illustrated embodiment, the second end 120 comprises a coil. The strain relief structure 116 is just one alternative embodiment of a strain relief structure, where the second end 120 is a coil which reduces or minimizes strain or kinking of the conduit after it is attached to the connector 102. Elastomeric properties of the alternative first end 118 allow the strain relief structure to couple with the connector when it exhibits a range of outer diameters, depending on wall thickness of the attached conduit 122. In another embodiment, the first end 118 of strain relief structure 116 may be configured to have mechanically varying inner profile that does not rely on elastomeric properties to accept larger and smaller structures due to the varying of the wall thickness or other transverse dimension of the conduit or the connector.

The strain relief structure 116 may thus reduce or minimize kinking or pinching of the conduit 122. In some embodiments, the strain relief structure 116 can include both a resilient characteristic and a soft inner surface. A non-limiting example is a springy material or configuration, such as a nitinol coil, to resist unwanted, unpredictable deformation in the zone of the strain relief structure 116. Also, a soft material or construction, such as a silicone sleeve can be provided to isolate the conduit 122 from pinching due to kinking. This sleeve may be shorter and configured to couple with a springy material, such as a nitinol coil, or it may be a longer sleeve configured to isolate the conduit 122 from pinching due to kinking without a springy material. In some embodiments the end user can slide the first end 118 of the strain relief structure 116 over a first end 114 of a connector 102 forming a friction fit with the ridges 109 of connector 102 and a slip fit with the conduit 122. In some embodiments, conduit 122 is inside first end 118 and both are sandwiched and secured by a connecting member. In some embodiments conduit 122 is secured inside first end 118 of the strain relief structure 116, against the ridges 109 of connector 102 by a connecting member by closing a first securing structure 112 pivotably coupled with flange 106 and a second securing structure 110 pivotably coupled with flange 106, to form a mechanical connection. In some embodiments first end 118 is an inner sleeve.

In at least the embodiments discussed above, the multiple-piece vascular access system 100, comprising a connector 102, at least one strain relief structure 116, and at least one conduit 122 may be coupled to create a continuous smooth lumen from one end of the conduit through the connector and out either the second end of the connector 104 or into another conduit.

In some embodiments, the inside diameter of first end 118 of the strain relief structure 116 may be sized just to accommodate the outside diameter of conduit 122. In these embodiments the pliability of 122 and/or the coefficient of friction with the material of first end 118 can make it difficult to slip conduit 122 through strain relief structure 116 and first end 118. In these embodiments, a suture, hemostat, or other tools may be used to allow an end user to pull the conduit through the strain relief structure, rather than push the potentially pliable conduit 122 against the friction of the first end 118. These methods are discussed in greater detail below.

Figure 2A:
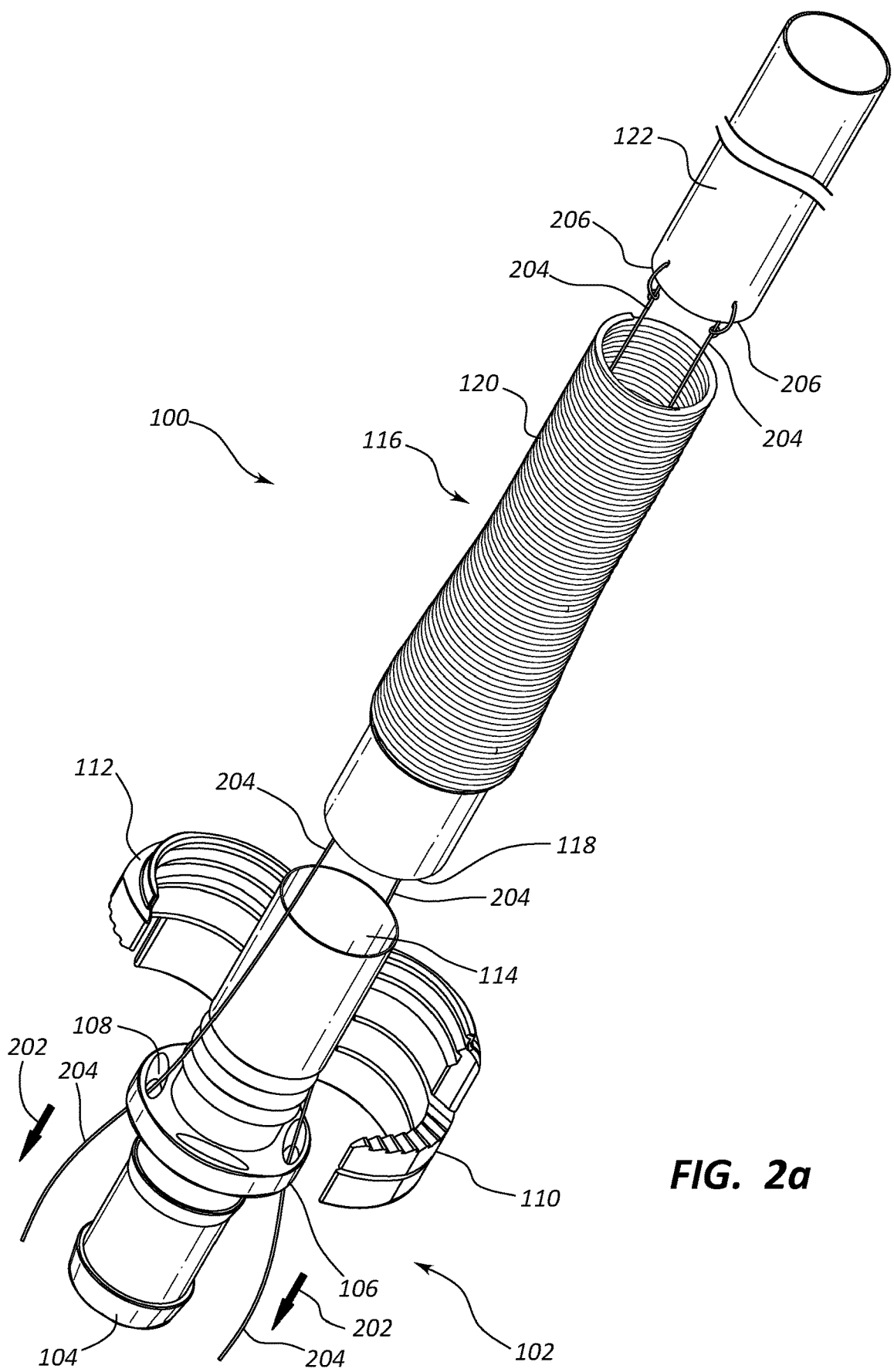
FIG. 2a is a simplified perspective view of a method of connecting components of a vascular access system.

FIG. 2a illustrates one embodiment of a method of connecting the components of a multi-piece vascular access system. At least one suture 204 is passed through a hole 108 in flange 106 of connector 102, then through the lumen of a strain relief structure 116 and connected to a first edge 206 of conduit 122. Tension 202 is applied to the at least one suture 204 to pull the conduit 122 into the strain relief structure 116 and over the first end 114 of connector 102 until the conduit 122 abuts up against flange 106. The strain relief structure 116 can then be slid over the conduit 122 until it is also abutting flange 106. In some embodiments, the conduit 122 is first pulled completely through 118 by suture 204 so that the first edge 206 can be fit over first end 114 of connector 102, and then an end user can slide first end 118 over top both conduit 122 and first end 114 of connector 102 so that 118 and 122 are flush up against flange 106.

Figure 2B:
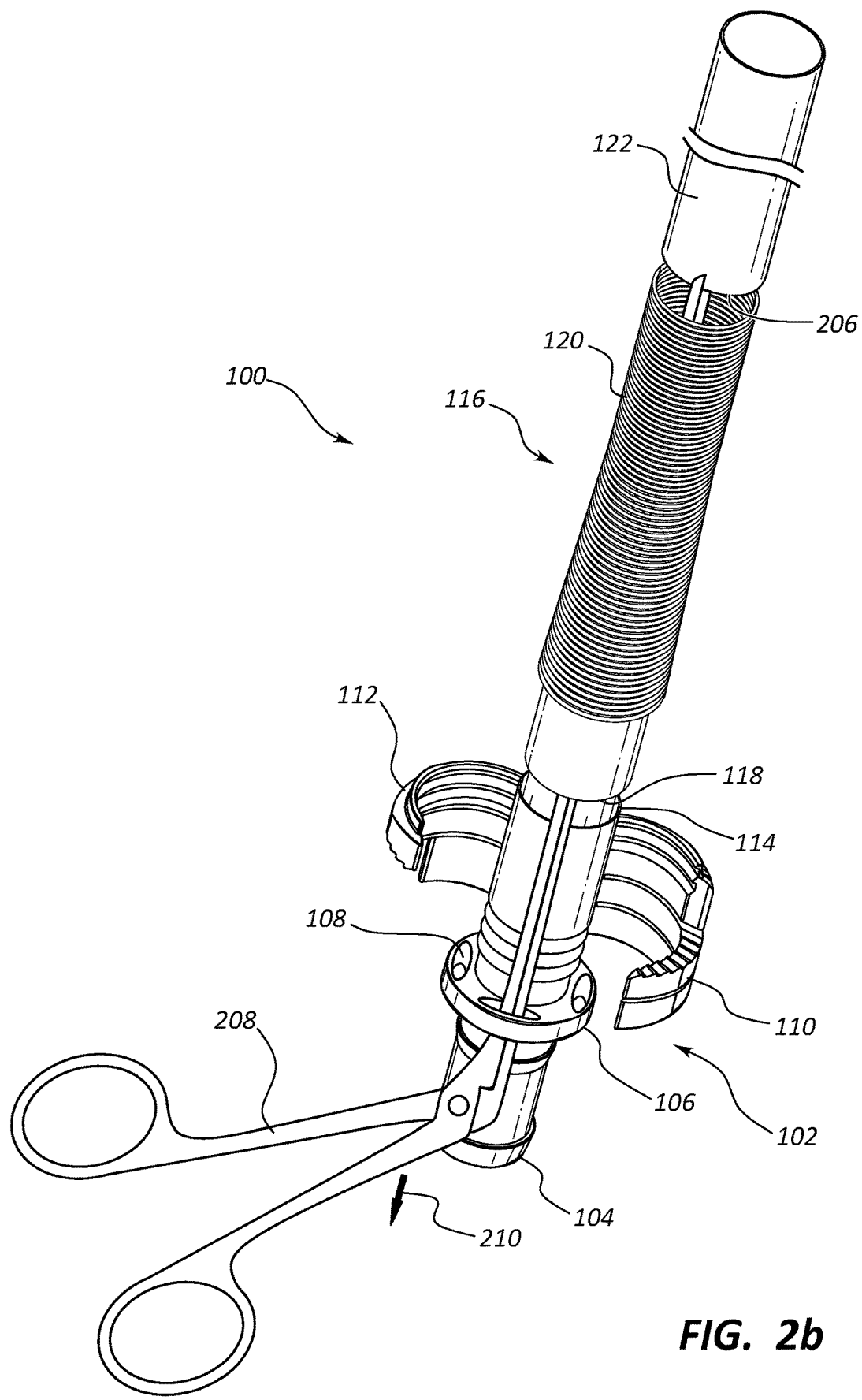
FIG. 2b is a simplified perspective view of another embodiment of a method of connecting components of a vascular access system.

FIG. 2b illustrates another embodiment of a method of connecting the components of a multi-piece vascular access system. In this embodiment, a grasping tool 208 is passed through a hole 108 in flange 106 of connector 102, then through the lumen of a strain relief structure 116 and first edge 206 of conduit 122 is grasped 212. Pulling force 210 is applied to the grasping tool 208 to pull the conduit 122 into the strain relief structure 116 and over the first end 114 of connector 102 until the conduit 122 abuts up against flange 106. The strain relief structure 116 can then be slid over the conduit 122 until it is also abutting flange 106. In some embodiments, the conduit 122 is pulled completely through 118 by grasping tool 208 so that the first edge 206 can be fit over first end 114 of connector 102, and then an end user can slide first end 118 over top both conduit 122 and first end 114 of connector 102 so that 118 and 122 are flush up against flange 106.

Figure 2C:
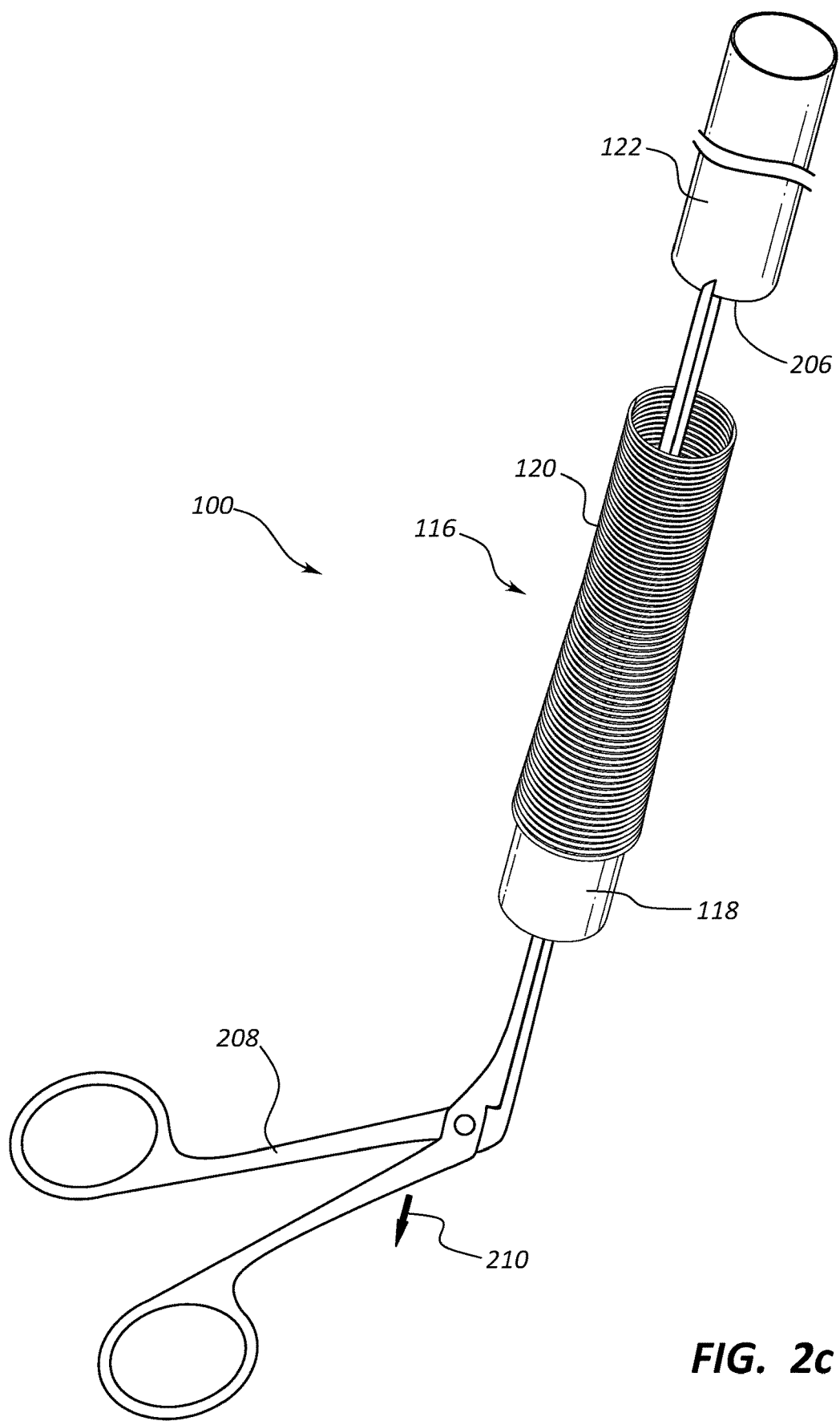
FIG. 2c is a simplified perspective view of yet another embodiment of a method of connecting components of a vascular access system.

FIG. 2c illustrates yet another embodiment of a method of connecting the components of a multi-piece vascular access system. In this embodiment, a grasping tool 208 is passed through the lumen of a strain relief structure 116 and first edge 206 of conduit 122 is grasped. Pulling force 210 is applied to the grasping tool 208 to pull the conduit 122 into the strain relief structure 116. In some embodiments, the conduit 122 is first pulled completely through 118 by grasping tool 208. An end user may then either use grasping tool 208 or manually slide first edge 206 over first end 114 of connector 102. In some embodiments the end user can then either manually or using grasping tool 208 slide first end 118 of strain relief structure 116 over top both conduit 122 and first end 114 of connector 102 so that 118 and 122 are flush up against flange 106.

Figure 3:
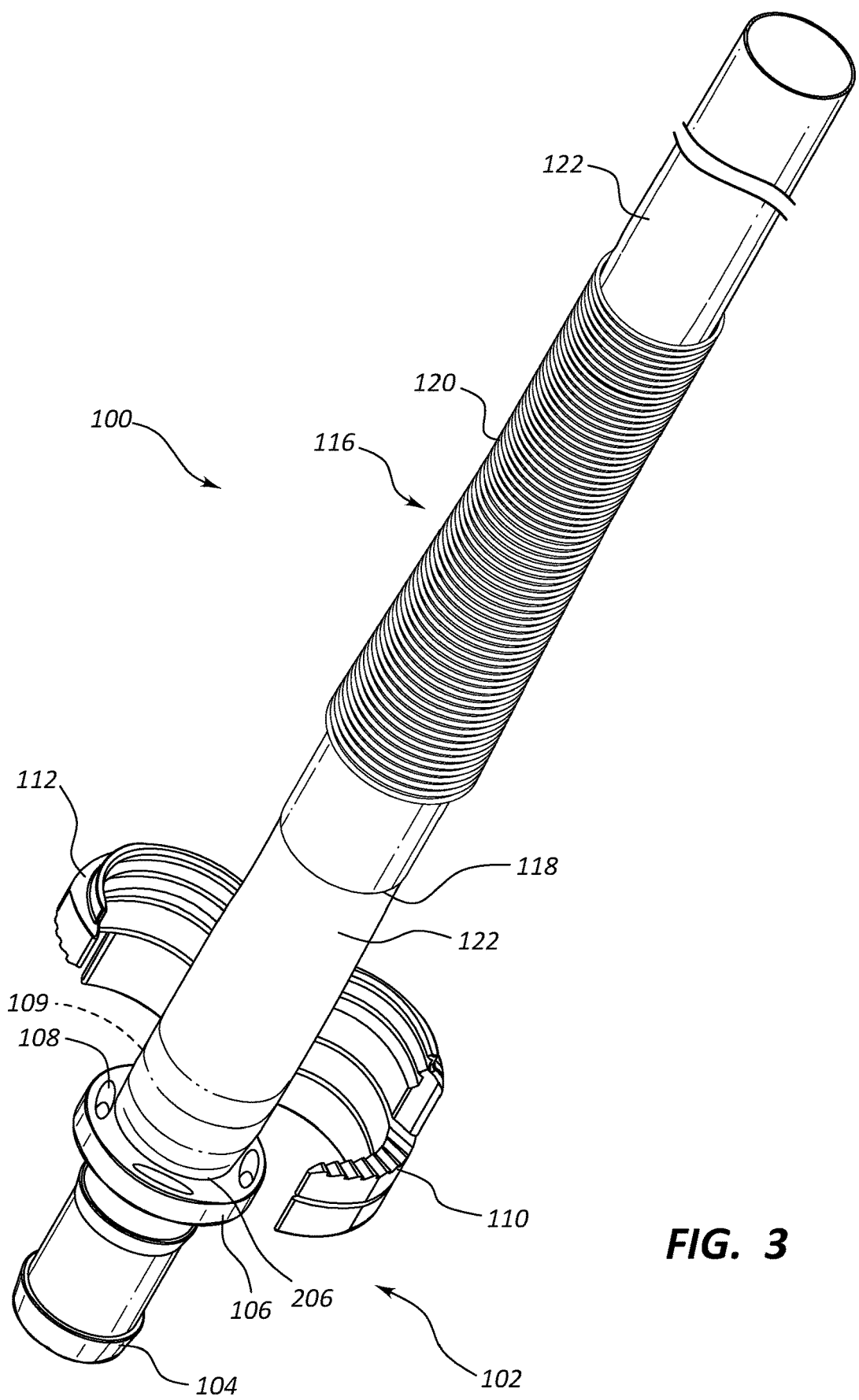
FIG. 3 is a simplified perspective view of a step in connecting components of a vascular access system.

FIG. 3 illustrates one embodiment of the method in which the conduit 122 has been slid over the first end 114 of connector 102 to abut up against flange 106. In some embodiments a suture, hemostat, or other tools may be used to open the lumen of conduit 122 which may make it easier to couple conduit 122 to connector 102. In some embodiments, the conduit 122 may have been manually pulled or pushed into a strain relief structure 116 such that the first edge 206 of conduit 122 is completely through the first end 118 of the strain relief structure 116. In other embodiments a suture, hemostat, or other tools may have been used to pull the conduit through the strain relief structure 116 until the first edge 206 of the conduit 122 is completely through the first end 118 of the strain relief structure 116. In some embodiments, the end user can then slide the first edge 206 of conduit 122 over top of the first end 114 of connector 102 to fit over the ridges 109 and abut against flange 106. In the embodiment illustrated in FIG. 3, the end user has not yet slid the strain relief structure 116 into a position abutting against flange 106, but instead slides freely over conduit 122.

Figure 4:
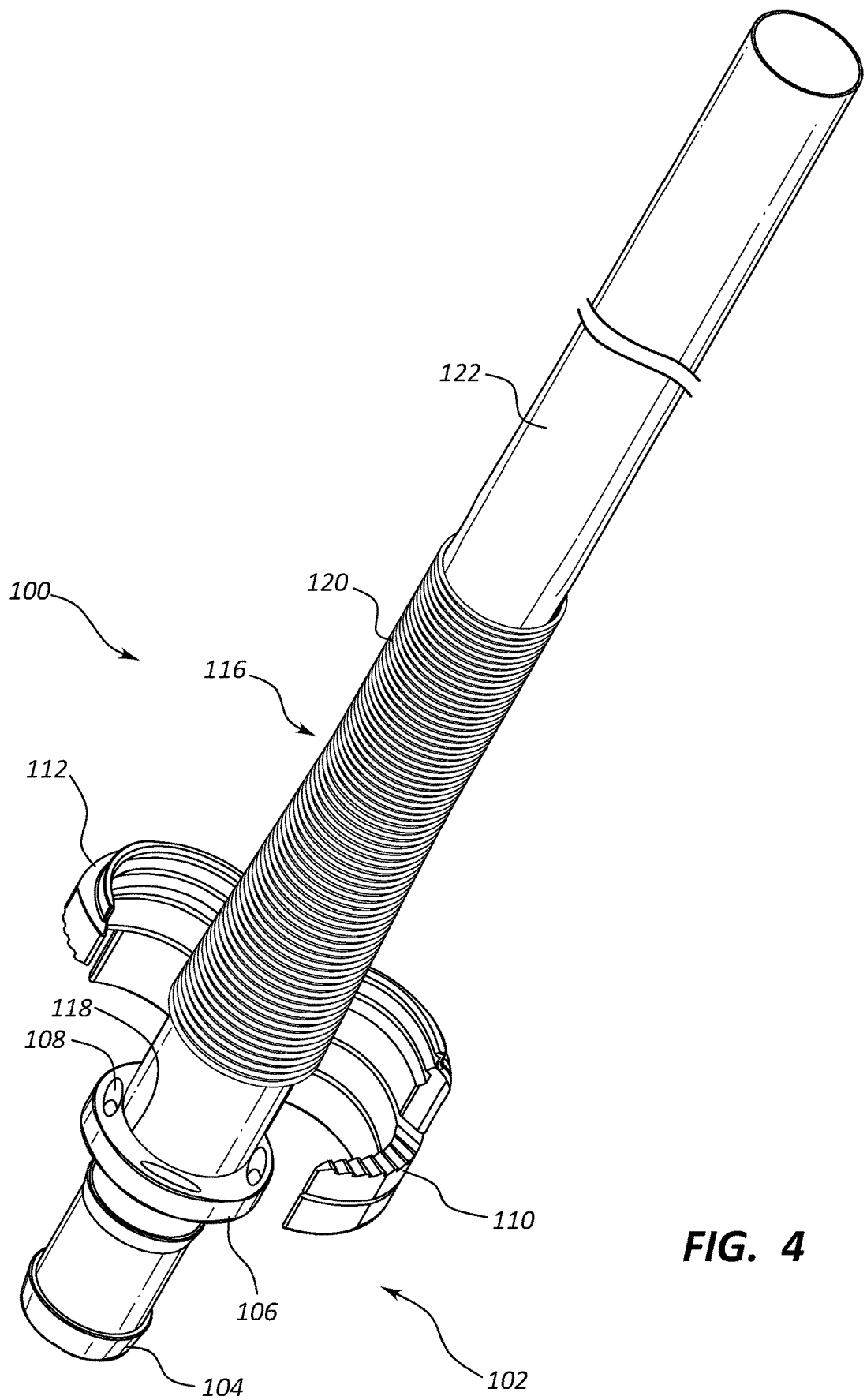
FIG. 4 is a simplified perspective view of another step in connecting components of a vascular access system.

FIG. 4 illustrates an embodiment in which an end user has already coupled conduit 122 over first end 114 of connector 102, as discussed above, and now the end user has positioned the strain relief structure 116 over top of the conduit 122, so that both strain relief structure 116 and conduit 122 abut up against flange 106. As discussed above, non-limiting examples of coupling the conduit 122, strain relief structure 116, and the connector 102 may include first coupling conduit 122 to the connector 102 either manually or using a suture, hemostat, or other tools before coupling the strain relief structure 116. In still other embodiments the conduit 122 and strain relief structure 116 may be coupled to connector 102 at the same time either manually or by using a suture, hemostat, or other tools. In some embodiments, the conduit 122 is pushed into or pulled into strain relief structure 116, the end user may then either manually or by using a suture, hemostat, or other tools, grasp both the conduit 122 and the first end 118 of strain relief structure together in order to slide them over first end 114 of connector 102. These embodiments result in the coupling of conduit 122, strain relief structure 116, and the connector 102 as depicted in FIG. 4.

Figure 5:
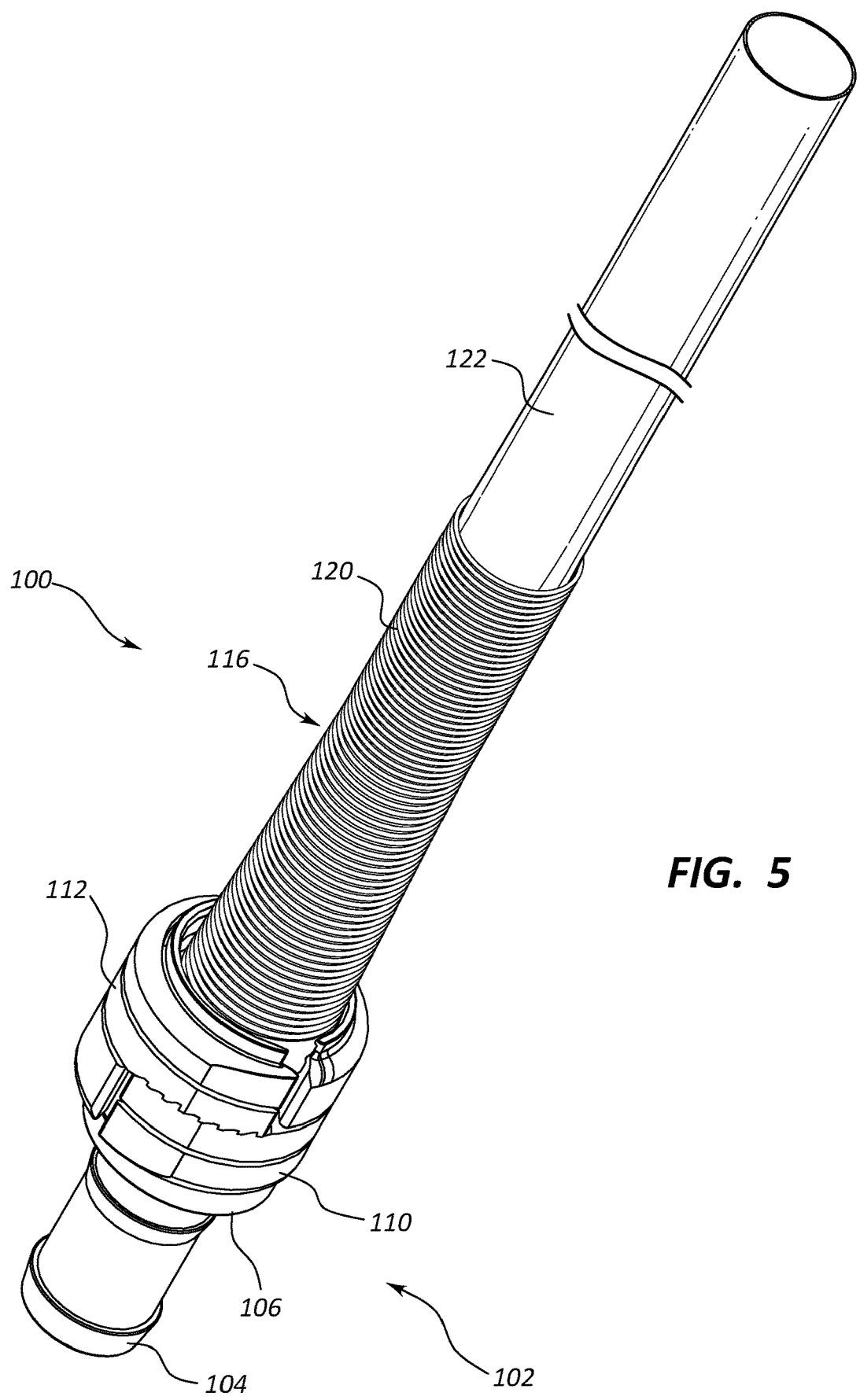
FIG. 5 is a simplified perspective view of another step in connecting components of a vascular access system.

FIG. 5 illustrates one embodiment of a connector 102 having connecting member comprising a first securing structure 112 pivotably coupled with flange 106 and a second securing structure 110 pivotably couple with flange 106, such that the two securing structures are in a closed configuration over the first end 114 of the connector 102 to securely fasten at least a conduit, such as conduit 122, and the first end 118 of the strain relief structure 116 to the connector 102, to form a mechanical connection between connector 102, strain relief structure 116, and conduit 122. This embodiment has one continuous smooth lumen running from conduit 122 through connector 102 and out of the second end 104 of connector 102.

Figure 6:
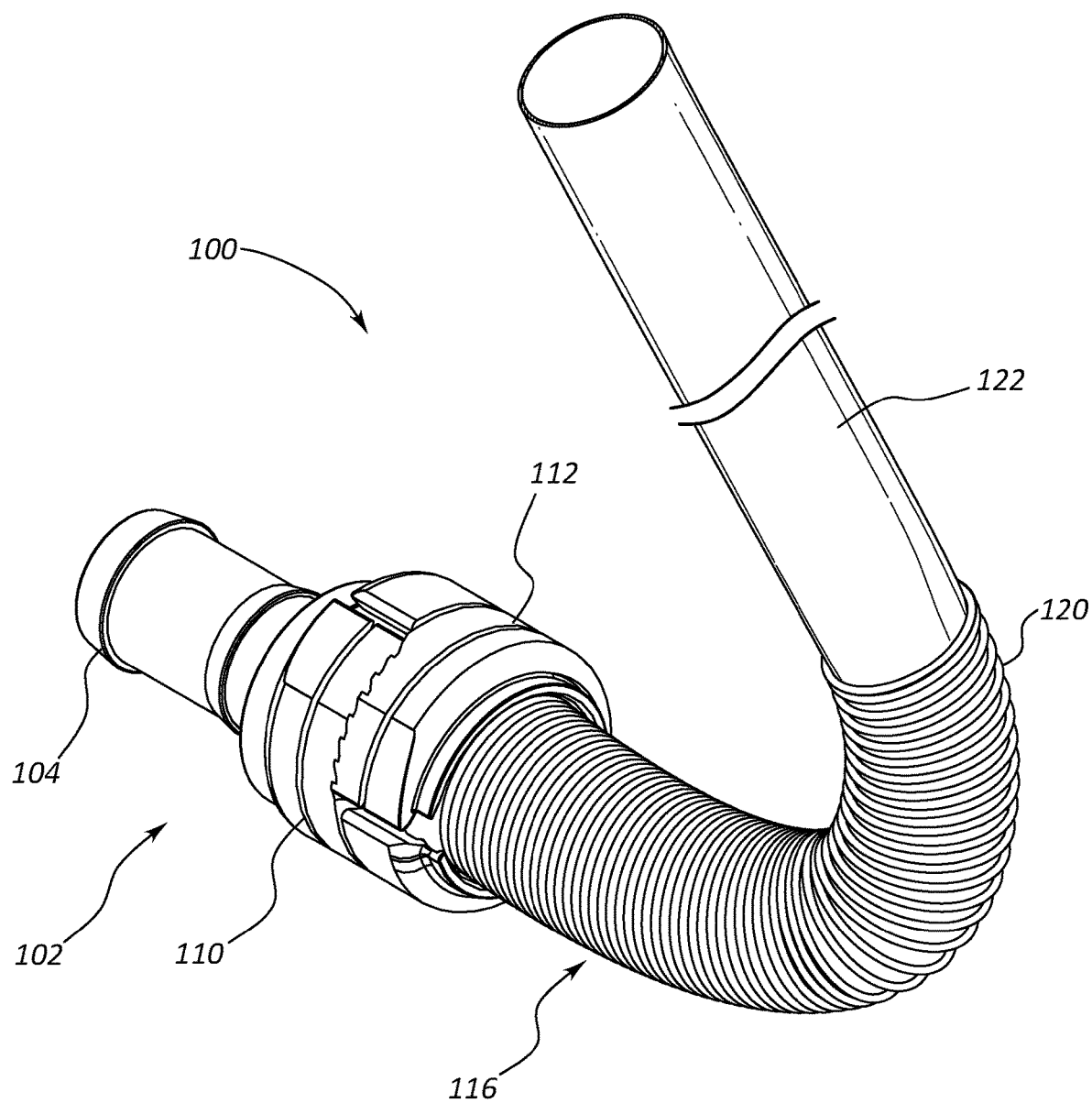
FIG. 6 is a simplified perspective view of the bending of a strain relief component of a vascular access system.

FIG. 6 illustrates the strain relief structure 116 preventing kinking or pinching of the conduit 122 after it is attached to connector 102. In this embodiment, the second end 120 may comprises a coil which reduces or minimizes strain or kinking of the conduit after it is attached to the connector 102. In some embodiments, the conduit 122 may be pliable, and without something like a strain relief structure 116, the conduit would pinch and kink at first end 114 of connector 102 if the conduit is ever at a similar angle to that depicted in FIG. 6. This pinching and kinking of the conduit 122 would great reduce the flow through the conduit 122, and disrupt the laminar flow through the conduit 122. As discussed herein, disruption to laminar flow and reduction in the flow rate would impair the function of the vascular access system 100.

The vascular access system 100 may comprise a plurality of different sized connectors 102 or connecting members configured to apply compressive force to sandwich a plurality of different sized outside diameter conduits 122 and different sized outside diameter strain relief structures 116. In some instances, the inside diameter of a given conduit does not correspond one-to-one with the outside diameter depending on the brand, manufacture, or material of the conduit. Toward this end having a means of determining the outside diameter of the plurality of components would benefit an end user performing a vascular access procedure. The ability to determine the outside diameter size of these different components may facilitate proper selection of connector such as connector 102. It may also help to determine if a particular conduit, graft, or catheter is compatible with a plurality of connectors or clamping structures. The devices and methods described below are non-limiting examples of determining which conduits and connectors to use.

Figure 7A:
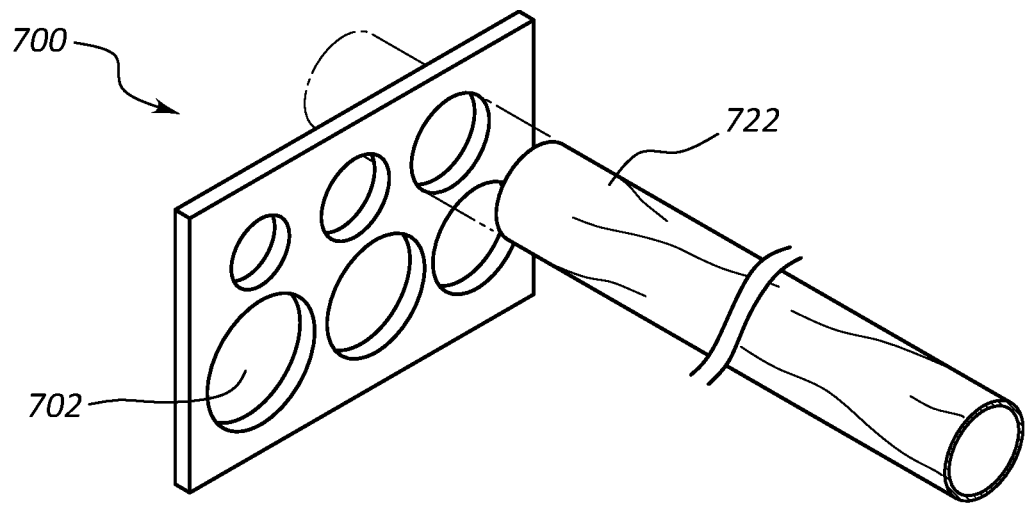
FIG. 7a is a simplified perspective view of a conduit outside diameter measurement apparatus.

FIG. 7a illustrates an embodiment of an outside diameter measurement apparatus 700. The apparatus 700 has a plurality of holes 702 with varying outside diameters which allow an end user to pass a conduit 722 into one of the holes 702 to obtain the outside diameter of the conduit. Once the end user determines the outside diameter of conduit 722, using an apparatus such as apparatus 700, the end user can then utilize one of a plurality of connectors, such as connector 102, in a kit which are configured to couple with the conduit 722 according to the disclosure in connection with FIGS. 1-6.

Figure 7B:
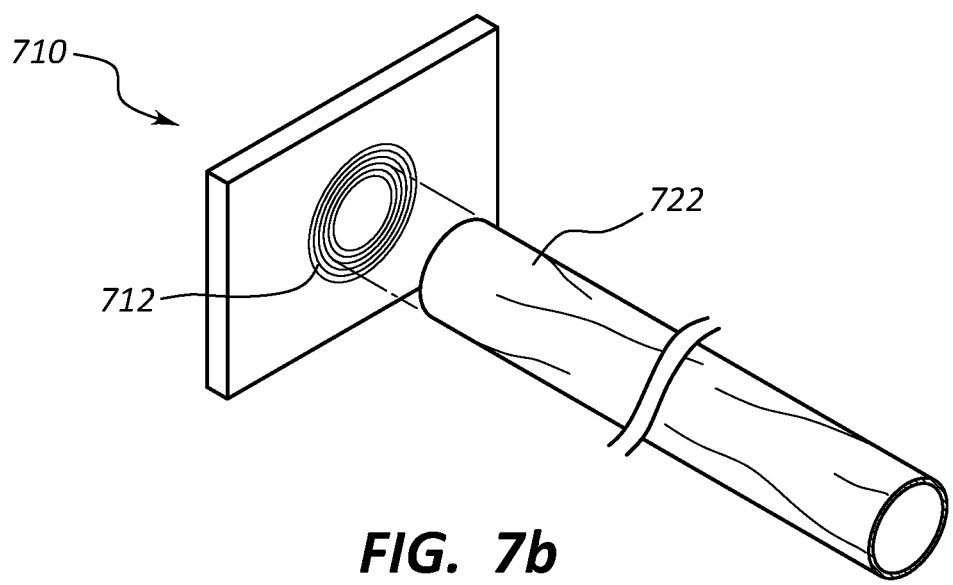
FIG. 7b is a simplified perspective view of another embodiment of a conduit outside diameter measurement apparatus.

FIG. 7b illustrates another embodiment of an outside diameter measurement apparatus 710. The apparatus 710 comprises a plurality of imprinted diameter measurements 712. An end user can compare an end of conduit 722 to the imprinted diameter measurements 712 to obtain the outside diameter of the conduit. Once the end user determines the outside diameter of conduit 722, using an apparatus such as apparatus 710, the end user can then utilize one of a plurality of connectors in a kit which are configured to couple with the conduit 722 according to the disclosure in connection with FIGS. 1-6.

Figure 8A:
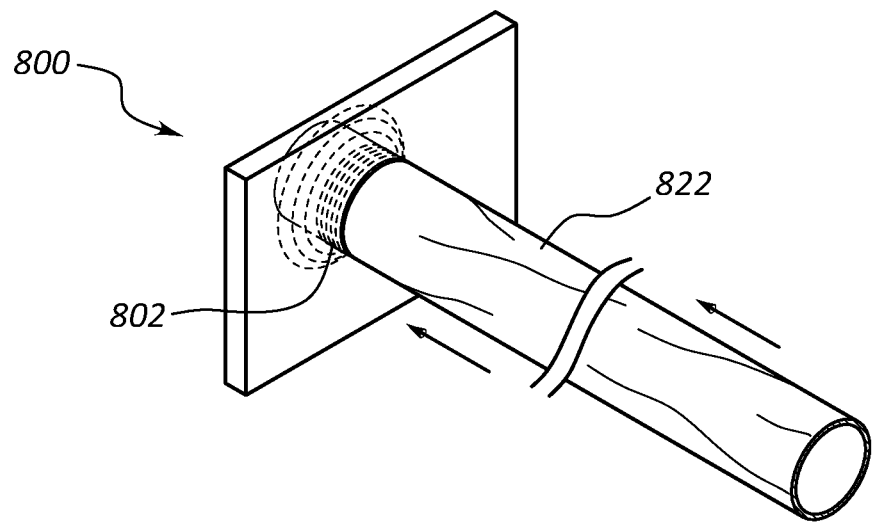
FIG. 8a is a simplified perspective view of another embodiment of a conduit outside diameter measurement apparatus.

FIG. 8a illustrates another embodiment of an outside diameter measurement apparatus 800. The apparatus 800 comprises a card with a spiral cut 802 through the thickness of the card. The varying diameters of the spiral cut 802 correspond to outside diameter measurements. An end user can depress a conduit 822 against the spiral cut which displaces one or more of the rings of the spiral cut, providing the end user with an outside diameter of the conduit 822. Once the end user determines the outside diameter of conduit 822, using an apparatus such as apparatus 800, the end user can then utilize one of a plurality of connectors in a kit which are configured to couple with the conduit 822 according to the disclosure in connection with FIGS. 1-6.

Figure 8B:
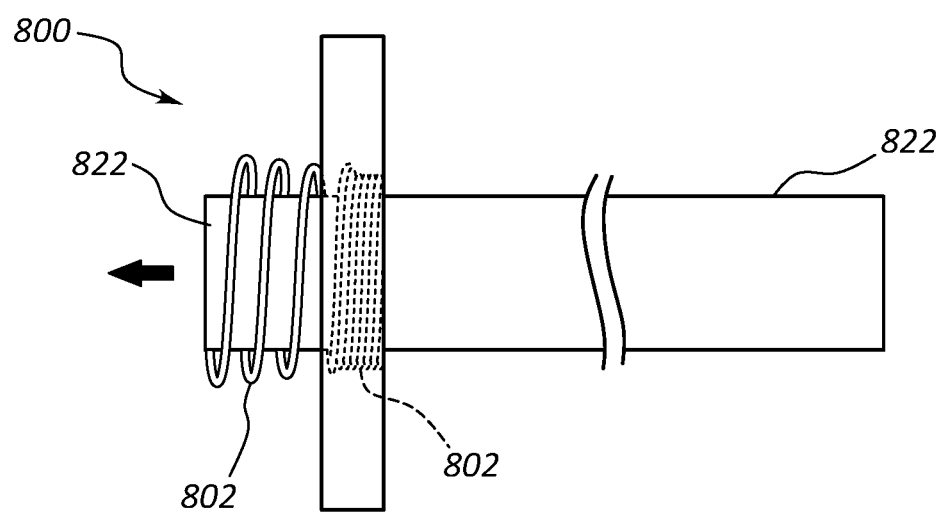
FIG. 8b is a simplified side view of another embodiment of a conduit outside diameter measurement apparatus.

FIG. 8b illustrates a side view of the apparatus 800. In this embodiment the end user has depressed conduit 822 through the spiral cut 802, displacing some of the rings 804, which provides the end user with the outside diameter of conduit 822.

Figure 9:
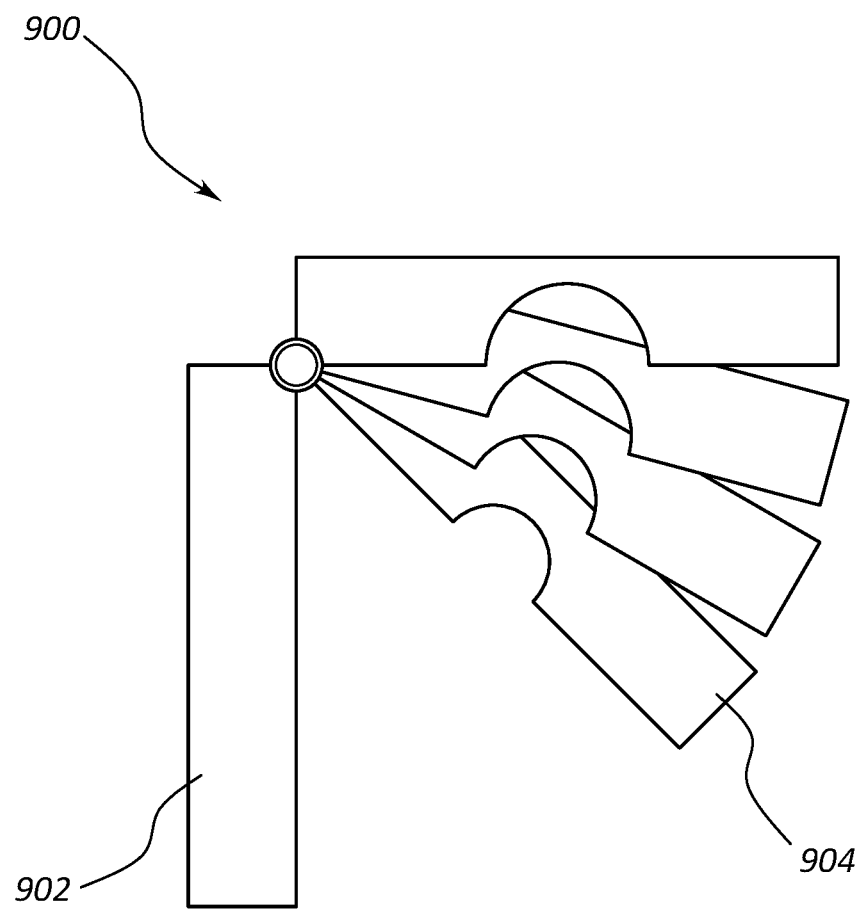
FIG. 9 is a simplified diagram of another embodiment of a conduit outside diameter measurement apparatus.

FIG. 9 illustrates a diagram of another embodiment of an outside diameter measurement apparatus 900. This apparatus comprises a first portion 902 which is pivotably coupled to a plurality of members 904 each with a different half crescent cut-away which correspond to a plurality of outside diameter measurements of a plurality of conduits. Once the end user determines the outside diameter of a conduit using an apparatus such as apparatus 900, the end user can then utilize one of a plurality of connectors in a kit which are configured to couple with the conduit according to the disclosure in connection with FIGS. 1-6.

Figure 10A:
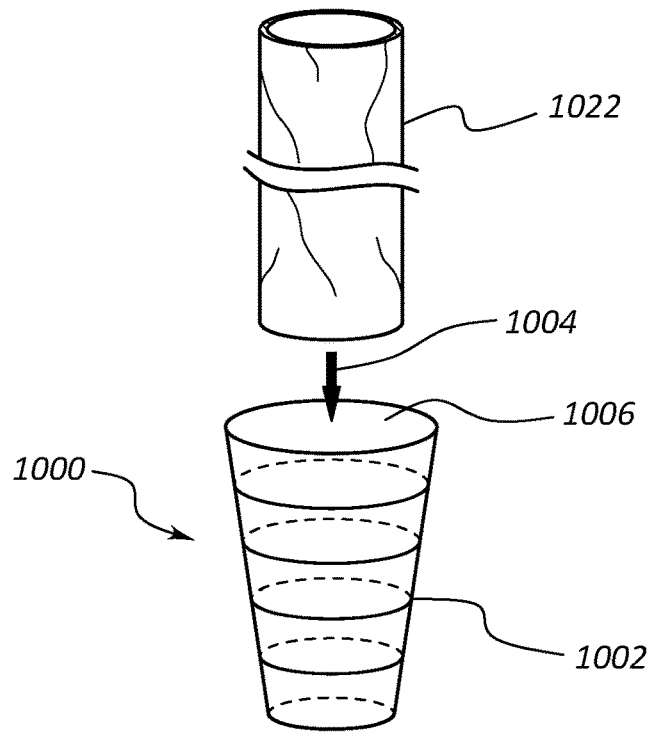
FIG. 10a is a simplified perspective view of another embodiment of a conduit outside diameter measurement apparatus.
Figure 10B:
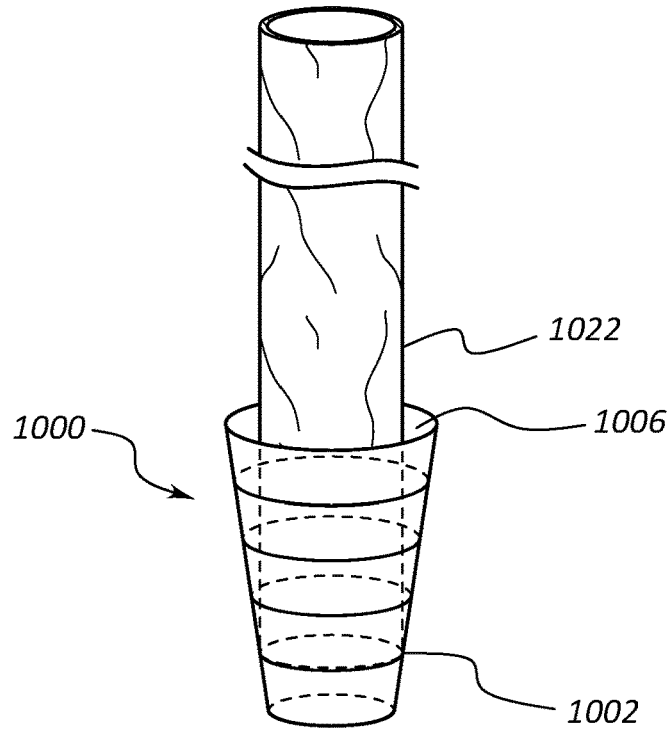
FIG. 10b is a simplified perspective view of a step of using another embodiment of a conduit outside diameter measurement apparatus.

FIGS. 10a and 10b. illustrate perspective views of another outside diameter measurement apparatus embodiment 1000. This apparatus comprises a tapered cone with at least one open end 1006, and a plurality of markings 1002 along the side. These markings 1002 correspond to various outside diameter measurements. An end user may place a conduit 1022 inside the open end 1006 until the conduit is flush with the side of the tapered cone. The end user can see how far down the conduit passes and use the markings 1002 to determine the outside diameter of the conduit 1022. Once the end user determines the outside diameter of conduit 1022, using an apparatus such as apparatus 1000 the end user can then utilize one of a plurality of connectors in a kit which are configured to couple with the conduit 1022 according to the disclosure in connection with FIGS. 1-6.

While the disclosure is susceptible to various modifications and implementation in alternative forms, specific embodiments have been shown by way of non-limiting example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

What is claimed is:

1. A vascular access kit comprising:
   a conduit outside diameter measurement apparatus comprising indicia; and a connector comprising a first securing structure and a second securing structure each pivotably coupled to the connector and together are configured to close over a first end of the connector, the connector configured to couple to a first end of a first artificial conduit with a first outside diameter and a first end of a strain relief by sandwiching the first end of the artificial conduit and the first end of the strain relief between a portion of the connector and the first and second securing structures such that there is a continual lumen through the first artificial conduit and the connector, wherein the indicia enable an end user to determine if the first artificial conduit and the strain relief are couplable with the connector when the first end of the artificial conduit and the first end of the strain relief are compared to the indicia, wherein the connector is one of a plurality of different sized connectors, wherein the conduit outside diameter measurement apparatus comprises a first portion pivotably coupled to a plurality of members that are substantially the same size and each with a different half crescent cut-away which corresponds to one of a plurality of outside diameter measurements, and wherein each half crescent cut-away is defined along a bottom edge of each plurality of members, the bottom edge of each plurality of members is coextensive with each other when the bottom edges of the plurality of members engage the first portion.

2. The vascular access kit of claim 1, wherein the indicia correlate to the plurality of different sized connectors.

3. The vascular access kit of claim 1, wherein the connector is configured to couple to a first end of a second artificial conduit with a second outside diameter, such that there is a continual lumen through the first artificial conduit, the connector, and the second artificial conduit.

4. The vascular access kit of claim 1, wherein the first artificial conduit is one of a plurality of different sized artificial conduits.

5. The vascular access kit of claim 4, wherein each one the different half crescent cut-aways is sized to match an outside diameter of a respective artificial conduit of the plurality of different sized artificial conduits.

6. The vascular access kit of claim 4, wherein each one of the plurality of different sized artificial conduits is configured to pass into a respective half crescent cut-away.

7. The vascular access kit of claim 4, wherein each one of the plurality of the different sized connectors is configured to couple with a respective artificial conduit of the plurality of the different sized artificial conduits.

* * * * *